United States Patent [19]

Grunberg

[11] 3,996,356

[45] Dec. 7, 1976

[54] COMPOSITION CONTAINING 5-SULFANILAMIDO-3,4-DIMETHYLISOXAZOLE AND A TRIMETHOXYBENZYL PYRIMIDINE

[75] Inventor: Emanuel Grunberg, North Caldwell, N.J.

[73] Assignee: Hoffmann-La Roche Inc., Nutley, N.J.

[22] Filed: Jan. 14, 1972

[21] Appl. No.: 217,959

Related U.S. Application Data

[63] Continuation-in-part of Ser. No. 838,635, July 2, 1969, abandoned, which is a continuation-in-part of Ser. No. 614,008, Feb. 6, 1967, abandoned.

[52] U.S. Cl. .................... 424/229; 424/251
[51] Int. Cl.$^2$ .............................. A61k 27/00
[58] Field of Search ................. 424/229, 251

[56] References Cited

UNITED STATES PATENTS

| | | | |
|---|---|---|---|
| 2,430,094 | 11/1947 | Wuest et al. | 424/229 |
| 2,909,522 | 10/1959 | Hitchings et al. | 424/229 |
| 3,341,541 | 9/1967 | Hotter | 424/229 |

FOREIGN PATENTS OR APPLICATIONS

| | | | |
|---|---|---|---|
| 671,981 | 5/1966 | Belgium | 424/229 |

OTHER PUBLICATIONS

Warner et al., Applied Microbiology, vol. 14, No. 2, Mar. 28, 1966, pp. 299 and 300.

*Primary Examiner*—Jerome D. Goldberg
*Attorney, Agent, or Firm*—Samuel L. Welt; Bernard S. Leon; R. Hain Swope

[57] ABSTRACT

Antibacterial compositions containing 5-sulfanilamido-3,4-dimethylisoxazole and 2,4-diamino-5-(3,4,5-trimethoxybenzyl)-pyrimidine are described.

5 Claims, No Drawings

COMPOSITION CONTAINING 5-SULFANILAMIDO-3,4-DIMETHYLISOXAZOLE AND A TRIMETHOXYBENZYL PYRIMIDINE

RELATED APPLICATIONS

This application is a continuation-in-part of United States patent application Ser. No. 838,635 filed July 2, 1969 now abandoned which in turn is a continuation-in-part of United States Patent Application Ser. No. 614,008 filed Feb. 6, 1967, now abandoned.

BRIEF SUMMARY OF THE INVENTION

A therapeutically active antibacterial composition comprising 5-sulfanilamido-3,4-dimethylisoxazole or a salt thereof with a pharmaceutically acceptable base and 2,4-diamino-5-(3,4,5-trimethoxybenzyl)-pyrimidine or a salt thereof with a pharmaceutically acceptable acid.

BACKGROUND OF THE INVENTION

The sulfonamide, 5-sulfanilamido-3,4-dimethylisoxazole and salts thereof with pharmaceutically acceptable bases, are known antibacterial compounds. Moreover, it is also known that various microorganisms, which are at first susceptible to treatment with said sulfonamide, as is the case with other well-known sulfonamides, develop a resistance which ultimately results in drugfast strains.

Accordingly, it was of particular interest to develop a combination of sulfonamide and activator which not only retards the development of the ultimate degree of resistance of strains of microorganisms to the sulfonamide but is also effective against such sulfonamide resistant strains. Unexpectedly, it has now been discovered that the combination of therapeutic compounds of this invention is medicinally effective in the chemotherapeutic treatment of bacterial infections which have been clinically demonstrated to be non-responsive to therapy with the sulfonamide alone.

2,4-diamino-5-(3,4,5-trimethoxybenzyl)-pyrimidine and a process for the preparation thereof are disclosed in U.S. Pat. No. 2,909,522. 5-sulfanilamido-3,4-dimethylisoxazole and a process for the preparation thereof are disclosed in U.S. Pat. No. 2,430,094.

DETAILED DESCRIPTION OF THE INVENTION

In its most comprehensive embodiment, the present invention relates to pharmaceutical compositions containing 5-sulfanilamido-3,4-dimethylisoxazole or a salt thereof with a pharmaceutically acceptable base and 2,4-diamino-5-(3,4,5-trimethoxybenzyl)pyrimidine or a salt thereof with a pharmaceutically acceptable acid.

In a more particular embodiment, the invention relates to pharmaceutical compositions, in suitable oral dosage forms, which compositions comprise 5-sulfanilamido-3,4-dimethylisoxazole or a salt thereof with a pharmaceutically acceptable base and 2,4-diamino-5-(3,4,5-trimethoxybenzyl)pyrimidine or a salt thereof with a pharmaceutically acceptable acid.

Still further embodiments of the invention reside in the formulation of pharmaceutical compositions into suitable oral dosage forms and in the use of such combinations in the treatment and control of bacterial infections which are non-responsive to therapy with 5-sulfanilamido-3,4-dimethylisoxazole or with 2,4-diamino-5-(3,4,5-trimethoxybenzyl)pyrimidine or their salts administered alone.

The term non-responsive infection in the language of the clinician and as used herein indicates an infection which will not respond to dosages ranging from the usual therapeutic dosage to the maximum recommended therapeutic dose of a chemotherapeutic agent consistent with safe medical practice. The compositions according to the present invention have unexpectedly been found to be effective in the treatment in vivo of bacterial infections which would not respond to either therapeutic agent administered alone. In addition, the compositions of the present invention have been unexpectedly found to be effective in retarding the development of resistance to 5-sulfanilamido-3,4-dimethylisoxazole therapy in vitro by certain bacteria such as *Proteus vulgaris*.

The expression pharmaceutically acceptable salts thereof utilized throughout the present specification denotes with regard to 5-sulfanilamido-3,4-dimethylisoxazole, salts formed utilizing suitable bases preferably an alkali metal base, such as sodium hydroxide, potassium hydroxide and the like.

The expression pharmaceutically acceptable salts thereof utilized throughout the present specification denotes with regard to 2,4-diamino-5-(3,4,5-trimethoxybenzyl)pyrimidine, salts formed utilizing suitable mineral acids such as hydrochloric acid, sulfuric acid, etc., and organic acids such as acetic acid, citric acid, lactic acid, maleic acid, salicylic acid and the like.

The compositions of this invention are prepared simply by admixing 5-sulfanilamido-3,4-dimethylisoxazole or a pharmaceutically acceptable salt thereof with a suitable base and 2,4-diamino-5-(3,4,5-trimethoxybenzyl)pyrimidine or a pharmaceutically acceptable salt thereof with a suitable acid.

The mixture is ultimately embodied into a suitable oral dosage form. For example, the compositions of this invention can be compressed by usual methods into single or multi-layer tablets. Moreover, the preparations can be produced in the form of coated tablets. Additionally, the preparations of this invention can be provided in the form of hard-shell capsules. In general, the various oral dosage forms of the present compositions are prepared by the conventional procedures and techniques of the art. The applicability of such methods and techniques to the formulation of the compositions of the present invention will be readily apparent to those skilled in the art.

It is also within the scope of this invention to administer each active component of the mixture individually. Thus, it is possible to formulate each of the components into separate dosage forms in accordance with procedures hereinbefore and hereinafter described for the combination.

In addition to the therapeutically active ingredients mentioned heretofore, the compositions of this invention can contain as optional ingredients any of the various adjuvants which are used ordinarily in the production of pharmaceutical preparations. Thus, for example, in formulating the present compositions into the desired oral dosage forms, one may use as optional ingredients, filler such as coprecipitated aluminum hydroxide-calcium carbonate, calcium phosphate dibasic or lactose; disintegrating agents such as maize starch; and lubricating agents such as talc, calcium stearate, etc. It should be fully understood, however, that the optional ingredients herein named are given by way of example only and that the invention is not restricted to the use hereof. On the contrary, other such adjuvants, the identify and use of which are well known in the art, can be, and are, employed in carrying out this invention.

The ratios in which the therapeutically active components are utilized in the preparations of this invention can be varied within rather wide limits. Generally, the compositions of the invention contain from about 1 to about 40 parts of 5-sulfanilamido-3,4-dimethylisoxazole or an equivalent amount of pharmaceutically acceptable salt thereof to one part of 2,4-diamino-5-(3,4,5-trimethoxybenzyl)pyrimidine or an equivalent amount of a pharmaceutically acceptable salt thereof, preferably from about 8 to about 30 parts of 5-sulfanilamido-3,4-dimethylisoxazole or an equivalent amount of a pharmaceutically acceptable salt thereof to one part of 2,4-diamino-5-(3,4,5-trimethoxybenzyl)-pyrimidine or an equivalent amount of a pharmaceutically acceptable uric salt thereof and most preferably 20 parts of 5-sulfanilamido-3,4-dimethylisoxazole or an equivalent amount of a pharmaceutically acceptable salt thereof to one part of 2,4-diamino-5-(3,4,5-trimethoxybenzyl)pyrimidine or an equivalent amount of a pharmaceutically acceptable salt thereof.

The composition of the present invention in a preferred unit dosage form will contain 500 mg. of 5-sulfanilamido-3,4-dimethylisoxazole or an equivalent amount of a pharmaceutically acceptable salt thereof and from about 25 mg. to about 50 mg. of 2,4-diamino-5-(3,4,5-trimethoxybenzyl)pyrimidine or an equivalent amount of a pharmaceutically acceptable salt thereof. However, it is also within the scope of this invention to utilize a unit dosage form which will contain from about 250 mg. to about 750 mg. of 5-sulfanilamido-3,4-dimethylisoxazole or an equivalent amount of a pharmaceutically acceptable salt thereof and from about 12.5 mg. to about 75 mg. of 2,4-diamino-5-(3,4,5-trimethoxybenzyl)pyrimidine or an equivalent amount of a pharmaceutically acceptable salt thereof.

The foregoing notwithstanding, it should be fully understood that the dosages set forth herein are exemplary only and they do not, to any extent, limit the scope of practice of the present invention.

The clinical efficacy of the compositions of the present invention is demonstrated by the following clinical trials.

A total of 88 male and female patients ranging in age from 18 to 78 years with chronic urinary infections were treated in three phases as follows:

Phase I:—all patients in the test received 1 gram of 5-sulfanilamido-3,4-dimethylisoxazole orally four times a day for from 10 to 14 days, in most cases 14 days.

Phase II:—the patients who showed no significant response to treatment with 5-sulfanilamido-3,4-dimethylisoxazole were given no medication for four days, then treated with 50 mg. of 2,4-diamino-5-(3,4,5-trimethoxybenzyl)pyrimidine orally four times a day for from 10 to 14 days, usually 14 days.

Phase III:—those patients exhibiting a non-responsive infection, e.g., no significant response to either the 5-sulfanilamido-3,4-dimethylisoxazole or the 2,4-diamino-5-(3,4,5-trimethoxybenzyl)pyrimidine therapy were given no medication for four days, then treated with a combination of 50 mg. of 2,4-diamino-5-(3,4,5-trimethoxybenzyl)pyrimidine and 1 gram of 5-sulfanilamido-3,4-dimethylisoxazole orally four times a day for from 10 to 14 days, usually 14 days.

The results of these successive treatments may be tabulated as follows.

| | Excellent No. of Patients | Good No. of Patients | Unsatisfactory (fair, poor, no response) No. of Patients | Not rated* No. of Patients |
|---|---|---|---|---|
| PHASE I 5-sulfanilamido-3,4-dimethylisoxazole | 36 | 5 | 44 | 3 |
| PHASE II 2,4-diamino-5-(3,4,5-trimethoxybenzyl)-pyrimidine | 17 | 3 | 23 | 2 |
| PHASE III 5-sulfanilamido-3,4-dimethylisoxazole plus 2,4-diamino-5-(3,4,5-trimethoxybenzyl)-pyrimidine | 12 | 6 | 5 | — |

*The patients not rated had to be dropped from the clinical trial for reasons unrelated to either their chronic urinary infection or the medication being administered during the trials.

The foregoing clinical study clearly establishes the therapeutic efficacy of the compositions of the present invention in the treatment of infections which are clinically non-responsive to treatment with either of the active components administered alone.

In addition to the foregoing clinical study in vivo tests have established that the compositions of the present invention are effective in combatting organisms which have exhibited resistance to treatment with 5-sulfanilamido-3,4-dimethylisoxazole administered alone. For example, Swiss albino mice infected with strains of *S. aureus Smith* and *P. vulgaris* 190 which had demonstrated a resistance to therapy with 5-sulfanilamido-3,4-dimethylisoxazole alone, e.g., the $CD_{50}$ was found to be 1000 mg/kg and greater than 2000 mg/kg, respectively, were found to be responsive to the following dosage of the compositions of the present invention: *S. aureus Smith* - 10 mg/kg of 2,4-diamino-5-(3,4,5-trimethoxybenzyl)pyrimidine and 100 mg/kg of 5-sulfanilamido-3,4-dimethylisoxazole; *P. vulgaris* 190 - 25 mg/kg of 2,4-diamino-5-(3,4,5-trimethoxybenzyl)pyrimidine and 189 mg/kg of 5-sulfanilamido-3,4-dimethylisoxazole. The treatment consisted of a single administration of medication per os daily for four days, with the first dosage administered 5–10 minutes after infection. The treatment in each case showed an activity increase for the compositions of the present invention of at least ten-fold over administration of 5-sulfanilamido-3,4-dimethylisoxazole alone.

The effectiveness of the compositions of the present invention as demonstrated above may be further observed in the aforedescribed clinical study wherein the presence of certain organisms was detected in individual patients and followed throughout the study. The results for five representative organisms may be tabulated as follows:

| Organism | Excellent – Good | | | Unsatisfactory (fair, poor, no response) | | |
|---|---|---|---|---|---|---|
| | Phase I | Phase II | Phase III | Phase I | Phase II | Phase III |
| A. aerogenes | 3 | 1 | 4 | 4 | 4 | — |
| E. coli* | 27 | 19 | 10 | 23 | 13 | 1 |
| Proteus | 5 | — | 2 | 6 | 5 | 2 |
| Strep (enterococcus) | 3 | 2 | 3 | 7 | 4 | 1 |
| Staph. aureus. | 2 | — | 2 | 2 | 2 | — |

Phase I - 5-sulfanilamido-3,4-dimethylisoxazole
Phase II - 2,4-diamino-5-(3,4,5-trimethoxybenzyl)pyrimidine
Phase III - 5-sulfanilamido-3,4-dimethylisoxazole plus 2,4-diamino-5(3,4,5-trimethoxybenzyl)pyrimidine

*In conducting the study, a total census of organisms was made without distinction as to whether the organism was observed initially before treatment was started. Therefore, in some cases the number of patients in Phases II and III is larger than the number of unsatisfactory responses in Phase I. This is due to emergence of the organism at some time during treatment. In the case of E. coli, there were two patients not rated in Phase III.

The unexpected potentiation of therapeutic activity of various compositions within the scope of the present invention may be demonstrated by the following in vivo study utilizing Proteus vulgaris 190 experimental infection in mice.

Swiss albino mice weighing from 18 to 20 g. were infected intraperitoneally with 100–1000 minimal lethal doses of Proteus vulgaris 190, obtained from an overnight broth culture to accomplish a lethal septicemic infection, inoculum was prepared in 5% hog gastric mucin.

Utilizing groups of 10 mice per dose, the animals were treated orally with 1.0 ml. of the desired concentration of therapeutic agent in 1% aqueous carboxymethyl cellulose solution. The $CD_{50}$ values for 5-sulfanilamido-3,4-dimethylisoxazole and 2,4-diamino-5-(3,4,5-trimethoxybenzyl)-pyrimidine, as well as combinations of 20, 30 and 40 parts, respectively, of 5-sulfanilamido-3,4-dimethylisoxazole to one part 2,4-diamino-5-(3,4,5-trimethoxybenzyl)-pyrimidine were determined. A total of six treatments with active ingredient were given as follows: two treatments 5 hours apart on the day of infection and the succeeding day and one treatment daily for two successive days thereafter. The observation period lasted 14 days. Heart blood of mice dying during this period was sampled and cultured on PDBB agar for the presence of infecting bacteria.

The minimum parameter to establish an acceptable potentiation in the activity of 5-sulfanilamido-3,4-dimethylisoxazole by the addition thereto of a given quantity of 2,4-diamino-5-(3,4,5-trimethoxybenzyl)-pyrimidine is a two-fold difference in the resulting $CD_{50}$ values. From the results set forth in the following Table it is evident that combinations of 20, 30 and 40 parts, respectively of 5-sulfanilamido-3,4-dimethylisoxazole to one part 2,4-diamino-5-(3,4,5-trimethoxybenzyl)-pyrimidine exhibited acceptable potentiation.

TABLE

| Active Ingredient | Ratio | $CD_{50}$ mg/kg | X-Fold Potentiation |
|---|---|---|---|
| Sulfisoxazole | — | 34 | — |
| Trimethoprim | — | 37 | — |
| Sulfisoxazole + Trimethoprim | 20:1 | 13 | 2.6 |
| Sulfisoxazole + Trimethoprim | 30:1 | 17 | 2.0 |
| Sulfisoxazole + Trimethoprim | 40:1 | 16 | 2.1 |

The capacity of the compositions of the present invention to greatly retard the development of the ultimate degree of drug resistance of Proteus vulgaris 190 may be demonstrated in vitro in the following experiment.

A strain of P. vulgaris 190 was rendered resistant to 5-sulfanilamido-3,4-dimethylisoxazole and 2,4-diamino-5-(3,4,5-trimethoxybenzyl)pyrimidine separately by growing the organism in test tubes containing the semi-synthetic medium of Adams and Roe (J. Bact., 49; 401, 1945) with decreasing concentrations of each of the agents made up by the serial dilution method. The development of resistance by the organism was noted by periodically determining the minimal amount of 5-sulfanilamido-3,4-dimethylisoxazole and 2,4-diamino-5-(3,4,5-trimethoxybenzyl)pyrimidine, respectively, which would inhibit the growth of the organism. The determination of minimum inhibitory concentration in all cases was carried out by incubation at 37° C. for 24 hours. The first tube showing good growth, e.g., where the concentration of the therapeutic agent present was ineffective in preventing growth of the organism, was utilized for the inoculation of a new experiment and so on for a total of 60 passages. The inoculum consisted of 0.05 ml. of a $10^{-3}$ dilution of the culture of P. vulgaris. Concurrently with the determination of the minimum inhibitory concentration of 5-sulfanilamido-3,4-dimethylisoxazole and 2,4-diamino-5-(3,4,5-trimethoxybenzyl)pyrimidine, a determination of minimum inhibitory concentration was made for 5-sulfanilamido-3,4-dimethylisoxazole in the presence of 2,4-diamino-5-(3,4,5-trimethoxybenzyl)-pyrimidine. For this determination, a constant concentration of 2,4-diamino-5-(3,4,5-trimethoxybenzyl)-pyrimidine was utilized and 5-sulfanilamido-3,4-dimethylisoxazole was added until minimum concentration was established. The concentration of 2,4-diamino-5-(3,4,5-trimethoxybenzyl) pyrimidine was approximately one-tenth the minimum inhibitory concentration of the compound alone and, as such, was considered to be for all practical purposes an inactive concentration. The minimum inhibitory concentration figures shown in the following table clearly illustrate the capacity of the compositions of the present invention to retard development of resistance by a microorganism to therapy with 5-sulfanilamido-3,4-dimethylisoxazole.

| | MINIMUM INHIBITORY CONCENTRATIONS VS. PROTEUS VULGARIS 190 | | |
|---|---|---|---|
| Passage Number | Concentration of 5-sulfanilamido-3,4-dimethylisoxazole mcg/ml | Concentration of 5-sulfanilamido-3,4-dimethylisoxazole mcg/ml in the presence of a constant concentration of 0.4 mcg/ml 2,4-diamino-5-(3,4,5-trimethoxybenzyl)pyrimidine | Concentration of 2,4-diamino-5-(3,4,5-trimethoxybenzyl)pyrimidine mcg/ml |
| 0 | 3.12 | 0.097 | 3.12 |
| 5 | 50 | 3.12 | 25 |
| 10 | 50 | 6.25 | 50 |
| 15 | 100 | 25 | 50 |
| 20 | 200 | 25 | 25 |
| 25 | 125 | 31.2 | 62.5 |
| 30 | 125 | 31.2 | 62.5 |
| 35 | 500 | 62.5 | 125 |
| 40 | 500 | 62.5 | 250 |
| 45 | 500 | 62.5 | 500 |
| 50 | 1000 | 125 | 1000 |
| 55 | 2000 | 125 | 1000 |
| 60 | 1000 | 62.5 | 1000 |

The invention will be better understood by reference to the following examples which are given for illustration purposes and are not meant to limit the invention.

Example 1

| Tablet formulation | Mg. per tablet |
|---|---|
| 5-sulfanilamido-3,4-dimethylisoxazole | 505 |
| 2,4-diamino-5-(3,4,5-trimethoxybenzyl)pyrimidine | 25.5 |
| Cornstarch | 30 |
| Lactose | 107.5 |
| Gelatin | 12 |
| Talcum | 15 |
| Magnesium stearate | 5 |
| Total | 700 |

Preparation:

505 Parts of 5-sulfanilamido-3,4-dimethylisoxazole, 25.5 parts of 2,4-diamino-5-(3,4,5-trimethoxybenzyl)pyrimidine and 107.5 parts of lactose were thoroughly mixed in suitable blending equipment and granulated with a solution containing 12 parts of gelatin. The moist mass was passed through a No. 12 screen and the granules were dried on paper-lined trays overnight. The dried granules were passed through a No. 14 screen and placed in a suitable mixer. Thereafter, 12 parts of talcum and 5 parts of magnesium stearate were added and blended. The granulation was compressed into tablets weighing approximately 700 mg. each, using punches having an approximate diameter of 12.7 mm. (½ inch). The final tablet thickness was about 5.35 mm.

Example 2

| Tablet formulation | Mg. per tablet |
|---|---|
| 5-sulfanilamido-3,4-dimethylisoxazole | 252.50 |
| 2,4-diamino-5-(3,4,5-trimethoxybenzyl)pyrimidine | 51.00 |
| Lactose | 86.50 |
| Cornstarch, U.S.P. | 60.00 |
| Prehydrolyzed cornstarch | 70.00 |
| Talcum | 15.00 |
| Cornstarch — U.S.P. — Dry | 10.00 |
| Magnesium stearate | 5.00 |
| Total | 550.00 |

Preparation:

252.5 Parts of 5-sulfanilamido-3,4-dimethylisoxazole and 51.00 parts of 2,4-diamino-5-(3,4,5-trimethoxybenzyl)pyrimidine, 86.50 parts of lactose, 60 parts of cornstarch U.S.P. and 70 parts of prehydrolyzed cornstarch were transferred to a suitable mixer and blended until uniform. The blended powders were passed through a Model D Fitzmill at high speed with hammers forward using a No. 00 screen. This premix was transferred to a suitable blender. The blended powders were granulated with distilled water. The wet granulation was passed through a Model D Fitzmill with knives forward at slow speed using a No. 4B screen. The milled, wet granules were dried at 110° F. The dry granules were passed through a Model D Fitzmill at medium speed with knives forward using a No. 12 screen. The milled, dry granulation was transferred to a suitable blender and 15 parts of talcum and 5 parts of magnesium stearate were added and mixed until uniform. The granulation was compressed on a BB2 Rotary. The punches used were 15/23 inches, flat beveled edge scored.

Example 3

| Tablet formulation | Mg. per tablet |
|---|---|
| 5-sulfanilamido-3,4-dimethylisoxazole | 505. |
| 2,4-diamino-5-(3,4,5-trimethoxybenzyl)pyrimidine | 51 |
| Cornstarch | 30 |
| Lactose | 82 |
| Gelatin | 12 |
| Talcum | 15 |
| Magnesium stearate | 5 |
| Total | 700 |

Preparation:

505 Parts of 5-sulfanilamido-3,4-dimethylisoxazole, 51 parts of 2,4-diamino-5-(3,4,5-trimethoxybenzyl)pyrimidine and 82 parts of lactose were thoroughly mixed in suitable blending equipment and granulated with a solution containing 12 parts of gelatin. The moist mass was passed through a No. 12 screen and the granules were dried on paper-lined trays overnight. The dried granules were passed through a No. 14 screen and placed in a suitable mixer. Thereafter, 12 parts of talcum and 5 parts of magnesium stearate were added and blended. The granulation was compressed into tablets weighing approximately 700 mg. each, using punches having an approximate diameter of 12.7 mm. (½ inch). The final tablet thickness was about 5.35 mm.

Example 4

| Capsule formulation | Mg. per capsule |
|---|---|
| 5-sulfanilamido-3,4-dimethylisoxazole | 250 |
| 2,4-diamino-5-(3,4,5-trimethoxybenzyl) pyrimidine | 25 |
| Lactose | 35 |
| Cornstarch | 35 |
| Magnesium stearate | 5 |
| Total | 350 |

Preparation:

250 Parts of 5-sulfanilamido-3,4-dimethylisoxazole, 25 parts of 2,4-diamino-5-(3,4,5-trimethoxybenzyl)-pyrimidine, 35 parts of lactose, 35 parts of cornstarch and 5 parts of magnesium stearate were mixed until thoroughly blended in a suitable size container. The powder was filled into No. 2, two piece, hard shell gelatin capsules to an approximate fill weight of 350 mg. using a Parke Davis capsulating machine.

Obviously, many modifications and variations may be made without departing from the spirit and the scope of this invention and therefore only such limitations should be imposed as indicated in the appended claims.

I claim:

1. An antibacterial therapeutic composition comprising from about 8 to about 30 parts of sulfonamide selected from the group consisting of 5-sulfanilamido-3,4-dimethylisoxazole and a pharmaceutically acceptable salt thereof with a suitable base and one part of a pyrimidine selected from the group consisting of 2,4-diamino-5-(3,4,5-trimethoxybenzyl)pyrimidine and a pharmaceutically acceptable salt thereof with a suitable acid.

2. A composition according to claim 1 comprises about 500 mg. of 5-sulfanilamido-3,4-dimethylisoxazole or a pharmaceutically acceptable salt thereof with a suitable base and from about 25 mg. to about 50 mg. 2,4-diamino-5-(3,4,5-trimethoxybenzyl)pyrimidine or a pharmaceutically acceptable salt thereof with a suitable acid.

3. A method for treating a human being host afflicted with a bacterial infection susceptible to sulfonamide treatment comprising administering to said host an antibacterially effective amount of a therapeutic composition comprising from about 8 to about 30 parts of a sulfonamide selected from the group consisting of 5 sulfanilamido-3,4-dimethylisoxazole and a pharmaceutically acceptable salt thereof with a suitable base and one part of a pyrimidine selected from the group consisting of 2,4-diamino-5-(3,4,5-trimethoxybenzyl)-pyrimidine and a pharmaceutically acceptable salt thereof with a suitable acid.

4. A method in accordance with claim 3 wherein said composition comprises about 20 parts of said sulfonamide for each part of said pyrimidine.

5. A method in accordance with claim 3 wherein said composition is administered orally in shaped dosage units, each unit comprising pharmaceutical adjunct material, about 500 mg. of 5-sulfanilamido-3,4-dimethylisoxazole or a pharmaceutically acceptable salt thereof with a suitable base and from about 25 mg. to about 50 mg. of 2,4-diamino-5-(3,4,5-trimethoxybenzyl)pyrimidine or a pharmaceutically acceptable salt thereof with a suitable acid.

* * * * *